United States Patent [19]

Teitelbaum

[11] Patent Number: 4,547,071
[45] Date of Patent: Oct. 15, 1985

[54] METHOD AND APPARATUS FOR MEASURING DENSITY GRADIENT

[75] Inventor: Heshel Teitelbaum, Ottawa, Canada

[73] Assignee: Canadian Patents and Development Limited, Ottawa, Canada

[21] Appl. No.: 393,827

[22] Filed: Jun. 30, 1982

[30] Foreign Application Priority Data

Nov. 19, 1981 [CA] Canada .................................... 390142

[51] Int. Cl.$^4$ ............................................. G01N 21/22
[52] U.S. Cl. ..................................... 356/344; 356/129
[58] Field of Search ............... 356/344, 128, 129, 130, 356/131, 138, 400, 427; 204/180 R, 299 R; 73/23.1, 61.1 C

[56] References Cited

U.S. PATENT DOCUMENTS

3,623,361 11/1971 Funk, Jr. ......................... 356/129 X
4,131,427 12/1978 Karp ............................... 356/129 X

FOREIGN PATENT DOCUMENTS

2847718 5/1979 Fed. Rep. of Germany ...... 356/400

OTHER PUBLICATIONS

Corno et al., "Differential Refractometry With Numerical Reading", Nouv. Rev. Optique Appliquee, t. 3, No. 2, pp. 81–84, 1972.

Ahlborn et al., "Quantitative Schlieren Densitometer Employing a Neutral Density Wedge", Rev. Sci. Instrum., vol. 47, No. 5, pp. 570–573, May 1976.

Primary Examiner—Davis L. Willis
Assistant Examiner—Matthew W. Koren

[57] ABSTRACT

The present invention related to a method and a device for use in measuring the gradient of density in a fluid. The device is comprised of a laser for providing a columnar light beam and a photodetector axially aligned with the laser. The photodetector detects the displacement of the light beam caused by the gradient of refraction of the fluid. A unit is provided for converting the displacement into an indication of the gradient of refraction and thereby the gradient of the density of the fluid. For density gradients caused by concentration gradients, an additional unit is provided for converting the displacement into a measure of the quantity of substances in the fluid.

14 Claims, 3 Drawing Figures

METHOD AND APPARATUS FOR MEASURING DENSITY GRADIENT

The present invention relates to a method and apparatus for measuring the rate of change or gradient of the density of a gas or liquid. More particularly, the present invention can measure rapid rates of change of the density of a specimen. Because the apparatus employs a laser for measuring the gradient of the index of refraction of a specimen, the physical co-ordinates of the point of measurement can be very accurately determined. This is particularly useful when the apparatus according to the present invention is used in conjunction with Electrophoresis, Ultracentrifuge and Chromatography methods for determining small quantities of substances contained in a liquid carrier.

The present invention is particularly useful in detecting small changes in the density of specimens since it is sensitive to the gradient of the index of refraction of a specimen which is directly proportional to the gradient of the density of the specimen. As is well known, the derivative of a function is a much more widely varying function than the function itself, especially about points of zero slope. Since it is often areas in the neighborhood of zero slope points of the density function that are of interest, the apparatus of the present invention is particularly sensitive.

A ray of light, travelling through a medium having a changing index of refraction, bends in the direction of increasing refractive index. The angle $\theta_y$ of this bend is equal to $l\partial n/\partial y$ where y is the direction of increasing refractive index, n is the density, and l is the thickness of the specimen traversed by the light ray.

A laser beam is used as the source of light rays and a photodetector, capable of measuring the deflection of the light rays through the angle $\theta$ is aligned with the laser beam. The specimen is located between the laser and the detector. The distance between the center of the specimen and the plane of the detector is set and designated as D. A distance $\Delta y$ is defined as the y component of the distance between the center points of the light beam in its nulled and deflected locations. The distance $\Delta y$ is proportional to the gradient of the index of refraction by the equaion D tan $\theta = \Delta y$. The angle $\theta$ will be small and for angles between 0° and 10°, tan $\theta \simeq \theta$. As a result, $y = D\theta_y = Dl\partial n/\partial y$.

There is a relation between the density of a gas or a liquid and the index of refraction n. It therefore can be seen that the distance $\Delta y$ can be related to the gradient of the density $\partial \rho/\partial y$ and that an apparatus according to the present invention can detect and measure the rate of change of the density in a specimen.

Such an apparatus can be directly used in conjunction with a wind tunnel for detecting the change in air density surrounding an object under test. In addition, other embodiments of the invention can be used in conjunction with electrophoresis or an ultracentrifuge or with cromatographs for determining the exact location of a density change within a specimen.

For example in electrophoresis, many different substances may be in solution in a liquid carrier, for example, water. A sample of the water containing the substances is placed in a vessel, preferably a square test tube, and is subjected to an electric field. Due to the ionic properties of the substances in the carrier, a migration and alignment of the various substances takes place within the test tube. Substances having certain densities will be located a certain distance from, say, the positive electrode. Tables have been prepared which indicate which substances will be located at which distances. As a result, it is important to determine the exact location of a change in density since such a density change at a particular location determines the presence of a particular substance in the carrier solution. The device of the present invention scans planes perpendicular to the electric field and detects small density changes at specific locations. These locations are translated into an identification of the substances and the magnitude of the deflections are translated into concentrations.

In the example of the ultracentrifuge, a solution containing unknown substances is spun at high speed. This separates the substances by density. The apparatus according to the present invention then scans the sample and determines, very accurately, the location of changes in density. The change in density locations can, by the use of tables or experiment, be used to determine the substance, or the distribution of substances according to their molecular weight.

In the example of chromatographic methods unknown substances absorbed on columns are eluted by a liquid or gas, and leave the chromatograph in succession. The time at which a particular substance leaves the column identifies the substance. According to the present invention, the apparatus remains fixed in space, and the flowing fluid provides an automatic scan of changes in fluid density indicating the presence of a substance, and its concentration.

In accordance with one aspect of the invention there is provided for use in measuring the gradient of density in a fluid, a device comprising: a laser for providing a columnar light beam; a photodetector axially aligned with said laser, said photodetector detecting the displacement of said light beam caused by the gradient of refraction of said fluid; and means for converting said displacement into an indication of the gradient of refraction and thereby the gradient of the density of said fluid.

In accordance with another aspect of the invention there is provided a method of measuring the gradient of the density in a fluid comprising the steps of: constraining said fluid within a vessel having opposite parallel transparent walls; impinging a substantially columnar beam perpendicular to one of said parallel walls; orienting a photodetector in a plane perpendicular to said beam and axially aligned therewith; detecting a beam displacement proportional to the gradient of the index of refraction of said fluid; and automatically equating said displacement with the gradient of the density of said fluid.

In accordance with another aspect of the invention there is provided a means of measuring the quantity of substance responsible for the density gradient, such means comprising two integrating devices.

In accordance with another aspect of the invention there is provided a method of measuring the quantity of the substance, comprising the steps of integrating said displacement twice with respect to the scanning distance.

The present invention will be described in detail hereinbelow with the aid of the accompanying drawings, in which.

Figure 1:
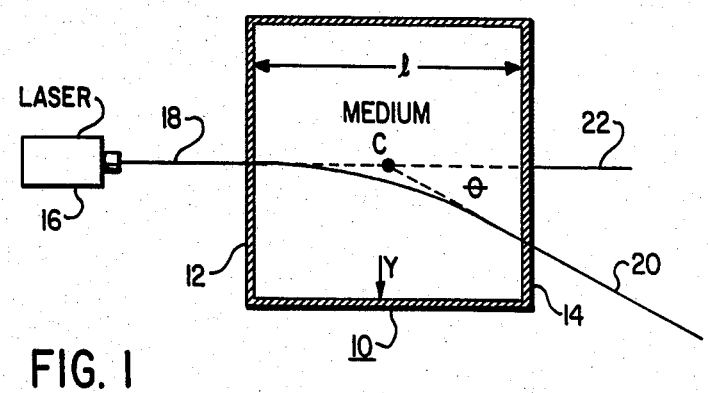
FIG. 1 is a schematic side elevation of a portion of the apparatus of the invention.

Referring to FIG. 1 a specimen medium, either liquid or gas, which has a changing density is constrained within a chamber 10 having transparent or at least semi-transparent side walls 12 and 14. For the sake of description, let the direction y be the direction of increasing refractive index.

A laser 16 is aligned to be perpendicular to the surface 12. Because it is perpendicular there is no refraction due to the interface with wall 12. A light ray 18 enters the specimen and is refracted along a curved path in the direction of increasing refractive index. The redirected beam 18 exists at wall 14 and proceeds to a detector (not shown) in a straight path 20. If the straight path is extrapolated to a point C, the mid point of the specimen chamber 10, it makes an angle $\theta$ with a path 22 of a light ray. The path 22 is the path which would have been followed had the specimen had no change in its refractive index. Interface refraction at chamber wall 14 can be ignored since $\theta$ is very small. This angle has been greatly exaggerated in the FIGURES for the sake of illustration. The angle $\theta y$ is equated to the partial derivative of the refractive index of the specimen in the y direction by $$\theta_y = l\partial n/\partial y \tag{1}$$

where l is the shortest path length of the beam 18 through the specimen.

In the example of electrophoresis a second electric field may be applied simultaneously in the Z-direction (points out of the plane of the paper in FIG. 1) perpendicular both to the y-direction and to the direction of the laser beam 22. The second field may be used to further separate two substances in a sample, with increased sensitivity.

Figure 2:
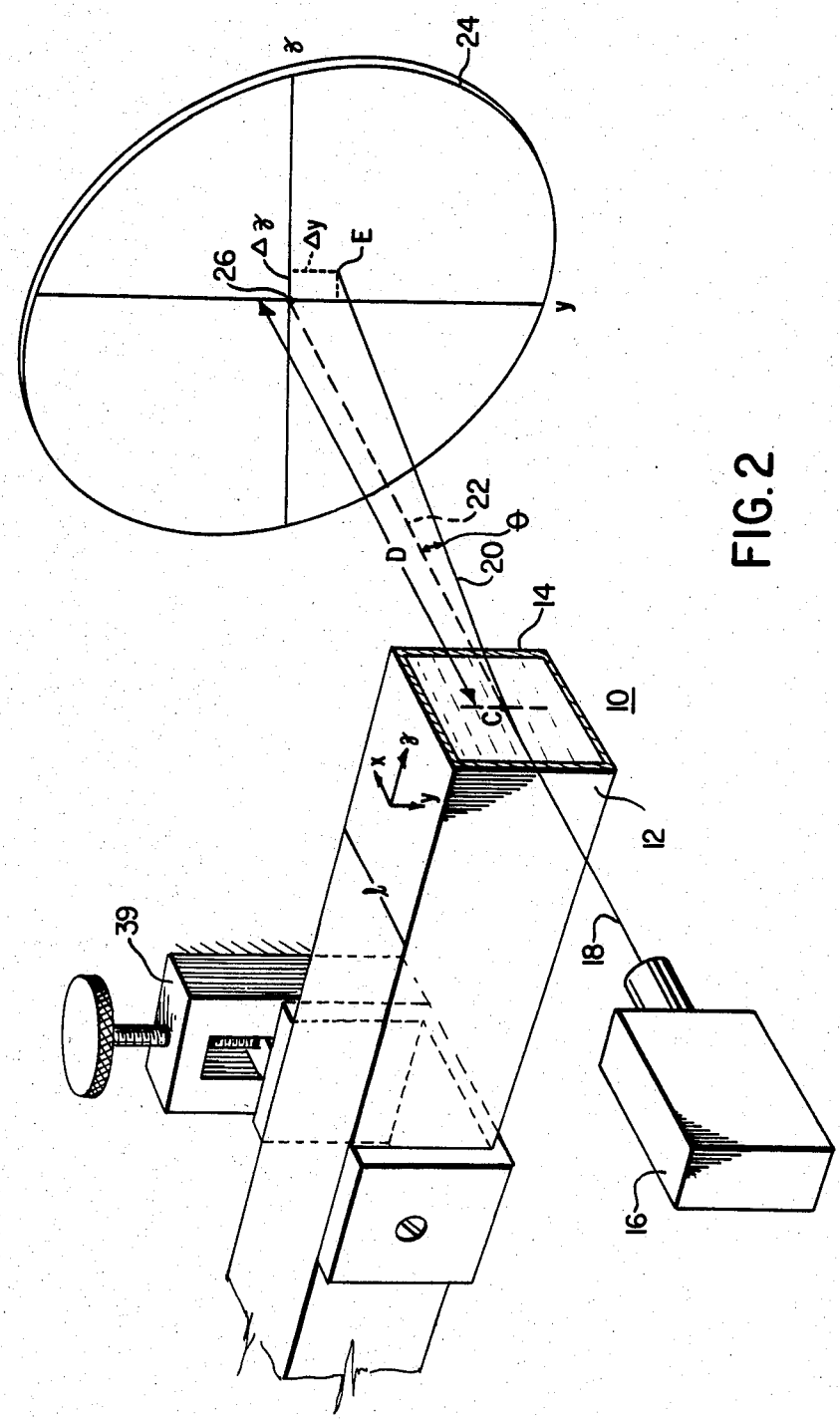
FIG. 2 is a perspective view of the apparatus of the invention.

Referring now to FIG. 2, wherein like elements have been designated with like reference numerals, a photodetector 24 has been located at a distance D from the center of the specimen chamber. The center 26 of the detector 24 is aligned with the center of the laser beam. The detector is aligned so that its surface is in the y-z plane and the unrefracted laser beam travels along the x axis in an orthogonal co-ordinate system. Changes in the index of refraction are detected in both the y and z directions simultaneously. Due to a changing refractive index in the y and z directions the light ray 20 contacts the detector 24 at point E. The change in the index of refraction in the y direction results in a displacement $\Delta y$ in the plane of the detector. Similarly the change in the index of refraction in the z direction results in a displacement of the beam by a distance $\Delta z$. The remainder of this description will be concerned only with the changes in the y direction, however, this is an arbitrary choice. The distance $\Delta y$ is given by $$\Delta y = D \tan \theta_y \tag{2}$$

For small angles of $\theta$ when dealing in radians $\theta \simeq \tan \theta$. Therefore for small angles of $\theta_y$ $$\Delta y = D\theta_y \tag{3}$$

substituting for $\theta_y$ from equation 1 we obtain $$\Delta y = Dl\partial n/\partial y \tag{4}$$

In a gas specimen the index of refraction and the density are related by the expression $$n = 1 + \beta\rho \tag{5}$$

where $\beta$ is the Gladstone-Dale constant and $\rho$ is the gas density.

Taking the partial derivative of n and $\rho$ with respect to the direction y, yields $$\partial n/\partial y = \beta \partial \rho/\partial y \tag{6}$$

and substituting $\partial n/\partial y$ in equation (4) results in $$\Delta y = Dl\beta \partial \rho/\partial y \tag{7}$$

As a result, from equation (7) it can be seen that the distance $\Delta y$ is directly equatable to the density gradient of the specimen. Also it should be noted that sensitivity or gain can be optically increased in the apparatus by simply increasing D, the distance between the center of the specimen and the plane of the detector.

A similar analysis provides the relationship between a rate of change of density of the specimen in the z direction and the distance $\Delta z$.

$$\Delta z = Dl\beta \partial \rho/\partial z \tag{8}$$

If the rate of change of density of a liquid is to be dealt with, the following is the relationship between index of refraction and density:

$$\frac{(n^2 - 1)}{(n^2 + 2)} = R\frac{\rho}{M} \tag{9}$$

where M is the molecular weight of the liquid and R is the molar refraction. If we take the partial derivative of n and $\rho$ with respect to the y direction we get:

$$\frac{6n}{(n^2 + 2)^2} \cdot \frac{\partial n}{\partial y} = \frac{R}{M} \frac{\partial \rho}{\partial y} \tag{10}$$

If water is the liquid of interest, n=1.33, M=18 and R=3.70 cm$^{-3}$. Equation (10) becomes $$\frac{\partial n}{\partial y} = 0.366 \frac{\partial \rho}{\partial y} \tag{11}$$

to a good approximation even when small quantities of substances are present in the water, if $\rho$ is in gm cm$^{-3}$ and y is in cm. Substituting for $\partial n/\partial y$ from (11) into (4), yields $$\Delta y = 0.366 Dl \partial \rho/\partial y \text{ (for water)} \tag{12}$$

From equation (12) it can be seen that there is a direct relationship between the movement of the center of the light beam through a distance $\Delta y$ and the gradient of the density $\partial \rho/\partial y$ in the y direction.

Figure 3:
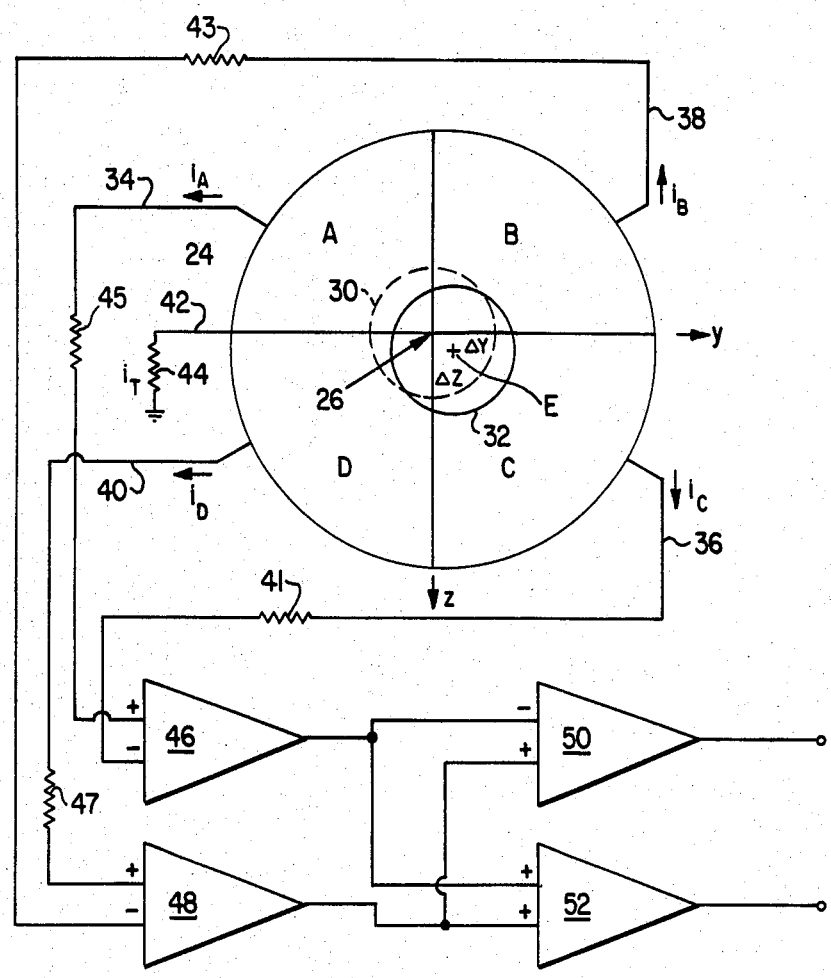
FIG. 3 is a schematic diagram of a detector and associated circuitry which go to make up a portion of the present invention.

The point E in FIG. 2 represents the center of the light beam transmitted by laser 16. In actual fact, the light beam forms a circular pattern of infinite diameter. However, most lasers have a cross sectional energy distribution which is gaussian and therefore can be thought of as circular beams having a finite diameter. FIG. 3 shows such a light beam imaged on photodetector 24 in the null position by a hatched circle 30 having a center located at position 26. The displacements Δy and Δz are small and it can be seen that the displaced beam 32 falls on all 4 quadrants A, B, C and D of the detector 24.

Photodetectors produce a current when subjected to a light source and the current is proportional to the light power distributed over that portion of the detector subjected to the light signal. Therefore, as the light beam 32 moves to a new center E on the detector of FIG. 3 the current $i_A$ flowing in lead 34 is reduced and the current $i_C$ flowing in lead 36 is increased. Similar current changes take place to $i_B$ and $i_D$ in leads 38 and 40, respectively. The sum of the 4 currents is equal to $i_T$ the total current which flows in lead 42 through resistor 44. Any change in total current is due only to absorption of the laser light by the specimen under test.

Leads 34, 36, 38 and 40 connect with the input terminals of differential amplifiers 46 and 48, respectively, through identical precision load resistors 41, 43, 45 and 47, each having a resistance of n ohms. The gains $G_1$ and $G_2$ of amplifiers 46 and 48, respectively, are adjustable and made equal to G. The output of amplifiers 46 and 48 are cross-connected with the inputs of differential amplifier 50 and summing amplifier 52, having gains $G_3$ and $G_4$, respectively.

The signal appearing at the output of differential amplifier 52 is $nGG_4[(i_A+i_D)-(i_C+i_B)]$ where $G_1$ and $G_2$ have been adjusted to G so that the output of amplifier 52 is related to left-right or Δy. Similarly, the output of summing amplifier 50 is $nGG_3[(i_D+i_C)-(i_A+i_B)]$ which is bottom-top or Δz. It can be seen that by manipulating the gain of the amplifiers the outputs can be directly relatable to $\partial \rho/\partial y$ and $\partial \rho/\partial z$.

The photodetector 24, the differential amplifiers 46, 48 and 50 and the summing amplifier 52, are designed to operate over a wide frequency range, i.e., from DC to 10 Mhz. This wide frequency range allows the detector to be sensitive to extremely rapid changes in the gradient of the density of the fluid under test.

As mentioned above, the present invention may be used in conjunction with electrophoresis or ultracentrifuge techniques. When this is done it is necessary to precisely move the specimen holder 10. Such movement is carried out in many well known ways and a means 39 is schematically shown in FIG. 2 for accomplishing this movement in the y direction. A similar means (not shown) could be included for movement in the z direction. With the electrophoresis technique the specimen holder and the electric fields are moved together. With ultracentrifuge techniques, the specimen is held vertically. With chromotographic techniques the specimen is held fixed in space; the fluid moving at speed u provides an automatic scan, so that the output signal is related to the rate of change of the density by $\partial \rho/\partial y = (\partial \rho/\partial t)/u$, where t is the time of flow.

The detector may be calibrated by scanning the laser beam across the photodetector at a known rate, by the use of, for example, a rotating mirror, and equating the rate of scan with the output signal. Such a scanning would result in a linear relationship $V = K\Delta y$ where V is the output voltage and K is the measured proportionality constant.

This relationship can be determined theoretically. When the beam is displaced from the centre of the detector by an amount b the voltage at the output of the detector is given by $$V = V_o \left[ \int_b^\infty f(y)dy - \int_{-\infty}^b f(y)dy \right] \quad (13)$$

where $V_o$ is the signal obtained when the laser beam is entirely on one quadrant of the detector, and may be determined directly from $i_T$.

When the beam is in the center of the detector the system is nulled and equation (13) is 0.

If the beam is moved in the y direction a known amount y then the output voltage is $$V = V_o \left[ \int_{-\Delta y}^\infty f(y)dy - \int_{-\infty}^{-\Delta y} f(y)dy \right] \quad (14)$$

A linear relationship exists for equation (14) when Δy is small. If f(y) is a normalized gaussian function of the power distribution of the laser beam along the y axis;

$$V = V_o \frac{\Delta y}{a} \sqrt{\frac{8}{\pi}}$$

where a is the gaussian beam "radius" to the $e^{-2}$ intensity point.

$$\text{If } K = \frac{V_o}{a} \sqrt{\frac{8}{\pi}} \text{ then } V = K\Delta y$$

which is the same function derived by physically scanning the detector along the y axis.

Use of this relationship along with equation (12) leads to $$V = 0.366 KlD \partial \rho/\partial y$$

for water as carrier. Using low noise electronics the sensitivity of this invention is limited by laser beam instability ($\simeq 0.1\%$). For a $\simeq 1$ mm, D$\simeq 10$ cm, l$\simeq 1$ cm, the minimum detectable gradient is $2.10^{-5}$ g cm$^{-4}$. This is superior by far to any known method. Linearity of response limits the maximum gradient ($V/V_o < 10\%$) to about 0.1 g cm$^{-4}$ if D is 2 cm. Spatial resolution is limited only by the ability of the analytical technique to actually separate the substances and by the precision of the positioning device ($\simeq 0.01$ mm). The width of the laser beam plays little role in determining the spatial resolution as it is the exact centre of the beam $\pm 1\%$ of "a" at the most which is involved in the beam deflection. The present invention works best when substances occupy a narrow region in the fluid. The narrower the region, the larger the gradient and hence the larger the signal.

Similar reasoning applies to gases, except that D can be as large as 10 m and l as large as 100 cm. Thus the sensitivity is even larger than for small liquid samples, as long as a telescope is included between sample and detector in order to minimize laser beam divergence.

The primary signal from the present invention is the local density gradient at the centre of the laser beam. In accordance with one aspect of this invention, the signal may be integrated electronically with respect to the scanned distance by well-known circuits, in order to obtain a measure of the local density. The resulting signal may be integrated a second time with respect to scanned distance (which can be considered to be scanned volume v if the cross-sectional area of the sample is constant). Since density is dm/dv, the resulting signal is a measure of the cumulative mass m of fluid sample. With due account of the solvent and other substances previously scanned, this results in a measure of the quantity of substance. A reference cell signal may be subtracted in order to continuously account for the solvent contribution. Part of the present invention includes two integrating devices and a display device such as a voltmeter or oscilloscope or strip chart recorder or computer processor.

I claim:

1. A device for measuring the gradient of density in a fluid, said device comprising:
   transparent container means for containing said fluid;
   a laser for providing a columnar light beam located on one side of said container means;
   a photodetector axially aligned with said laser on the other side of said container means, said photodetector detecting the displacement of said light beam caused by the gradient of refraction of said fluid;
   said photodetector being comprised of four pie-shaped segments oriented in a plane perpendicular to said beam forming a circular array, each of said segments producing a current which is proportional to the surface area of said segment impinged by said beam; and
   means connected to said photodetector for converting said displacement into an indication of the gradient of refraction and thereby the gradient of the density of said fluid.

2. The device according to claim 1, wherein said container means is oriented with respect to said beam so that said beam enters said container means perpendicular to its surface.

3. The device according to claim 2, further including means for precisely moving said container means in directions which are orthogonal and perpendicular to the axis of said light beam.

4. The device according to claim 1, 2 or 3, wherein said laser generates said light beam having a gaussian energy distribution.

5. The device according to claim 1, wherein said photodetector includes first, second, third and fourth output terminals, each output terminal being connected to one of said four segments in a one-to-one correspondence.

6. The device according to claim 5, wherein said photodetector further includes a fifth terminal connected to a voltage biasing circuit or to all four of said segments, said fifth terminal being connected so as to carry the total current generated by all four segments.

7. The device according to claim 5, wherein said means for converting includes first, second and third differential amplifiers and a summing amplifier and wherein said first and third output terminals are connected to said first differential amplifier and wherein said second and fourth output terminals are connected to said second differential amplifier, the outputs of said first and second differential amplifiers being simultaneously connected to the input of said third differential amplifier and said summing amplifier, the output of said third differential amplifier representing the displacement of said beam in a first orthogonal direction perpendicular to said beam, the output of said summing amplifier representing the displacement of said beam in a second orthogonal direction perpendicular to said beam.

8. The device according to claim 7, wherein said photodetector, said first, second and third differential amplifiers and said summing amplifier operate from DC to a high frequency.

9. The device according to claim 8, wherein said high frequency is 10 Mhz.

10. The device according to claim 1, wherein said fluid is a liquid and the gradient of the density is related to the gradient of the index of refraction by the expression $$\frac{6n}{(n^2+2)^2} \frac{\partial n}{\partial y} = \frac{R}{M} \frac{\partial \rho}{\partial y}$$

wherein n is the index of refraction of the liquid, M is the molecular weight of the liquid, $\rho$ is the density of the liquid, y is an orthogonal direction perpendicular to said beam, and R is the molar refraction of the liquid.

11. The device according to claim 1 wherein said fluid is a gas and the gradient of the density is related to the gradient of the index of refraction by the expression $$\partial n/\partial y = \beta \partial \rho/\partial y$$

wherein n is the index of refraction of the gas, $\rho$ is the density of the gas, $\beta$ is the Gladstone-Dale constant and y is an orthogonal direction perpendicular to said beam.

12. The device according to claim 1 further including means for converting said displacement into a quantitative measure of the mass of a substance changing the density of said fluid.

13. An electrophoresis apparatus which includes an electric field including the device according to claim 1 further comprising means for producing a second electric field perpendicular to the electric field of the electrophoresis apparatus.

14. A method of measuring the gradient of the density in a fluid and the quantity of substances in said fluid comprising the steps of:
   constraining said fluid within a vessel having opposite parallel transparent walls;
   impinging a substantially columnar beam perpendicular to one of said parallel walls;
   orienting a photodetector in a plane perpendicular to said beam and axially aligned therewith;
   detecting a beam displacement proportional to the gradient of the index of refraction of said fluid;
   automatically equating said displacement with the gradient of the density of said fluid;
   scanning said beam over a distance along said one of said parallel walls;
   twice integrating the displacement of said beam with respect to said scanning distance, such integration being proportional to the mass of scanned fluid and being related to the mass of one of said substances in said fluid;
   automatically equating said integration with the quantity of substances in said fluid; and
   displaying the density gradient of said fluid and the mass of said substance on a recording device.

* * * * *